United States Patent
Nakamura

(12) 
(10) Patent No.: US 6,635,664 B1
(45) Date of Patent: Oct. 21, 2003

(54) INSECTICIDE COMPOSITIONS AND METHOD FOR DESTROYING INSECTS

(75) Inventor: Satoshi Nakamura, Minoo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/111,315

(22) PCT Filed: Oct. 16, 2000

(86) PCT No.: PCT/JP00/07172

§ 371 (c)(1), (2), (4) Date: Apr. 24, 2002

(87) PCT Pub. No.: WO01/30152

PCT Pub. Date: May 3, 2001

(30) Foreign Application Priority Data

Oct. 26, 1999 (JP) ............................................ 11-303959

(51) Int. Cl.[7] ........................ A01N 43/40; A01N 43/78
(52) U.S. Cl. ........................ 514/345; 514/370; 514/327
(58) Field of Search ................................ 514/327, 370, 514/345

(56) References Cited

U.S. PATENT DOCUMENTS 4,751,225 A    6/1988  Nashida et al. ............. 514/277

FOREIGN PATENT DOCUMENTS

| EP | 0 376 279 A2 | 7/1990 |
|---|---|---|
| EP | 0 549 441 A1 | 6/1993 |
| EP | 0 979 606 A1 | 2/2000 |
| JP | 60-215671 A | 10/1985 |

*Primary Examiner*—Dwayne C. Jones
(74) *Attorney, Agent, or Firm*—Birch, Stewart, Kolasch & Birch, LLP

(57) ABSTRACT

A pesticidal composition comprising 4-phenoxyphenyl 2-(2-pyridyloxy)propyl ether and (E)-1-(2-chlorothiazol-5-ylmethyl)-3-methyl-2-nitroguanidine as active ingredients, especially, the composition having the weight ratio of 4-phenoxyphenyl 2-(2-pyridyloxy)propyl ether and (E)-1-(2-chlorothiazol-5-ylmethyl)-3-methyl-2-nitroguanidine in the composition is in the range of from 100:1 to 1:30. Further, a method for controlling pests applying an effective amount of 4-phenoxyphenyl 2-(2-pyridyloxy)propyl ether and (E)-1-(2-chlorothiazol-5-ylmethyl)-3-methyl-2-nitroguanidine to pest or place where pest inhabits.

9 Claims, No Drawings

INSECTICIDE COMPOSITIONS AND METHOD FOR DESTROYING INSECTS

This application is the national phase under 35 U.S.C. §371 of PCT International Application No. PCT/JP00/07172 which has an International filing date of Oct. 16, 2000, which designated the United States of America.

TECHNICAL FIELD

The present invention relates to pesticidal compositions and pesticidal methods.

BACKGROUND ARTS

Hitherto, pesticides for controlling various pests such as agricultural and forestry pests, ectoparasites of animals and hygienically unfavorable pests have been developed. However, it cannot be said that old pesticides exhibit satisfactory effects in the practical use wherein pests in various growth stages exist.

The present invention provides pesticidal compositions and pesticidal methods which are very effective for controlling the pests in agricultural and forestry fields, such as whiteflies, and further effective for controlling ectoparasites of animals, hygienically unfavorable pests and the other various pests.

DISCLOSURE OF THE INVENTION

According to the present invention, a pesticidal composition comprising 4-phenoxyphenyl 2-(2-pyridyloxy)propyl ether and (E)-1-(2-chlorothiazol-5-ylmethyl)-3-methyl-2-nitroguanidine as active ingredients and a pesticidal method comprising utilizing 4-phenoxyphenyl 2-(2-pyridyloxy) propyl ether and (E)-1-(2-chlorothiazol-5-ylmethyl)-3-methyl-2-nitroguanidine together give satisfactory effect in practical use.

Namely, the present invention provides a pesticidal composition (hereinafter, referred to as the present pesticidal composition) comprising 4-phenoxyphenyl 2-(2-pyridyloxy)propyl ether (hereinafter, referred to as pyriproxyfen) and (E)-1-(2-chlorothiazol-5-ylmethyl)-3-methyl-2-nitroguanidine (hereinafter, referred to as chlothianidine) as active ingredients and a pesticidal method (hereinafter, referred to as the present pesticidal method) comprising utilizing pyriproxyfen and chlothianidine together.

Pyriproxyfen used in the present pesticidal composition and the present pesticidal method is a compound described in U.S. Pat. No. 4,751,225 specification and chlothianidine is a compound described in U.S. Pat. No. 5,034,404 specification. These compounds can be produced according to the descriptions in these specifications.

The combination of pyriproxyfen and chlothianidine produces a synergistic effect that is clearly larger than a sum of the sole effect of each compound as shown in the test examples described later.

In the present pesticidal composition and the present pesticidal method, pyriproxyfen and chlothianidine are combined and utilized in a ratio that can produce a synergistic effect. It is usually 0.01 to 30 parts by weight of chlothianidine, preferably 0.5 to 10 parts by weight based on 1 part by weight of pyriproxyfen.

The present pesticidal composition and the present pesticidal method can be applied for controlling various pests such as agricultural and forestry pests, ectoparasites of animals and hygienically unfavorable pests. Examples of the pest include arthropods such as insects and acarina and nematoda, namely Hemipteran pests such as Delphacidae (planthoppers) [e.g. *Laodelphax striatellus* (small brown planthopper), *Nilaparvata lugens* (brown planthopper) and *Sogatella furcifera* (white-backed rice planthopper)], Deltocephalidae (leafhoppers) [e.g. *Nephotettix cincticeps* and *Nephotettix virescens*], Aphididae (aphids) [e.g. Aphis gossypii (cotton aphids), Myzus persicae (green peach aphid), *Aphis citricola, Lipaphis pserudobrassicae* (turnip aphid), *Nippolachnus piri*, Toxoptera aurantii (black citrus apid) and *Toxoptera ciidius* (brown citrus apid)], stink bugs [e.g. Nezara antennata (green stink bug), *Cletus punctiger, Riptortus clavetus* (bean bug) and *Plautia stali* (oriental stink bug)], Aleyrodidae (whiteflies) [e.g. *Trialeurodes vaporariorum* (greenhouse whitefly), *Bemisia tabaci* (sweetpotato whitefly) and *Bemisia argentifolli* (silverleaf whitefly)], scales [e.g. *Aonidiella aurantii* (California red scale), *Comstockaspis perniciosa* (San Jose scale), *Unaspis citri* (citrus snow scale), *Pseudaulacaspis pentagona* (white peach scale), *Saissetia oleae* (brown olive scale), *Lepidosaphes beckii* (purple scale), *Ceroplastes rubens* (red wax scale) and *Icerya purchasi* (cottonycushion scale)], Tingidae (lace bugs) and Psyllidae (suckers); Lepidopteran pests such as Pyralidae [e.g. *Chilo suppressalis* (rice stem borer), *Cnaphalocrocis medinalis* (rice leafroller), *Ostrinia nubilalis* (European cornborer), *Parapediasia teterrella* (bluegrass webworm), *Notarcha derogata* (cotton leafroller) and *Plodia interpunctella* (Indian meal moth)], Noctuidae [e.g. *Spodoptera litura* (tobacco cutworm), Pseudaletia separata (rice armyworm), *Mamestra brassicae* (cabbage armyworm), *Agrotis ipsilon* (black cutworm), Trichoplusia spp., *Heliothis* spp. and Helicoverpa spp.], Pieridae [e.g. *Pieris rapae*], Tortricidae [e.g. Adoxophyes spp., Grapholita molesta (oriental fruit moth) and *Cydia pomonella*], Carposinidae [e.g. *Carposina niponensis* (peach fruit moth)], Lyonetiidae [e.g. Lyonetia spp.], Lymantriidae [e.g. Lymantria spp. and Euproctis spp.], Yponameutidae [e.g. *Plutella xylostella*], Gelechiidae [e.g. *Pectinophora gossypiella* (pink bollworm)], Arctiidae (tiger moths) [e.g. Hyphantria cunea (fall webworm)] and Tineidae [e.g. *Tinea translucens* (casemaking clothes moth) and *Tineola bisselliella* (webbing clothes moth)]; Dipteran pests such as Culex spp. [e.g. *Culex pipiens pallens* and *Culex tritaeniorhynchus*], Aedes spp. [e.g. *Aedes albopictus*], Anopheles spp. [e.g. Anopheles sinensis], Chironomidae (midges), Ceratopogonidae (biting midges) [e.g. *Culicoides oxystoma*], Muscidae [e.g. *Musca domestica* (housefly) and *Muscina stabulans* (false housefly)], Calliphoridae, Sarcophagidae, Fannia spp. (little house flies), Anthomyiidae [e.g. Delia platura (seedcorn maggot) and *Delia antiqua* (onion maggot)], Tephritidae (fruit flies), Drosophilidae (vinegar flies), Psychodidae (sand flies), Simuliidae (black flies), Tabanidae, Stomoxyidae (stable flies) [e.g. Haematobia irritans] and Agromyzidae (leafminer flies); Coleopteran pests such as corn rootworms [e.g. *Diabrotica virgifera* virgifera (western corn rootworm) and *Diabrotica undecimpunctata howardi* (southern corn rootworm)], Scarabaeidae [e.g. *Anomala cuprea* and *Anomala rufocuprea*], Curculionidae (weevils) [e.g. *Sitophilus zeamais* (maize weevil), *Lissorhoptrus oryzophilus* (ricewater weevil), *Hypera pastica* (alfalfa weevil) and *Callosobruchuys chienensis* (adzuki bean weevil)], Tenebrionidae (darkling beetles) [e.g. *Tenebrio molitor* (yellow mealworm) and *Tribolium castaneum* (red flour beetle)], Chrysomelidae (leaf beetles) [e.g. *Aulacophora femoralis* (cucurbit leaf beetle), *Phyllotreta striolata* (striped flea beetle) and *Leptinotarsa decemlineata* (Colorado beetle)], Anobiidae, Epilachna spp. [e.g. *Epil-*

*achna vigintioctopunctata*], Lyctidae (powderpost beetles), Bostrychidae, Cerambycidae and *Paederus fuscipes*; Dictyopteran pests such as *Blattella germanica* (German cockroach), *Periplaneta fuliginosa* (smokybrown cockroach), *Periplaneta americana* (American cockroach), *Periplaneta brunnea* (brown cockroach) and *Blatta orientalis*; Thysanopteran pests such as *Thrips palmi, Thrips tabaci, Thrips hawaiiensis* (flower thrips), *Scirtothrips dorsalis* (yellow tea thrips), *Frankliniella intonsa* (flower thrips), *Frankliniella occidentalis* (western flower thrips) and *Ponticulothrips diospyrosi*; Hymenopteran pests such as Formicidae (ants), Vespidae (hornets), Bethylidae and Tenthredinidae (sawflies) [e.g. *Athalia japonica* (cabbage sawfly)]; Orthopteran pests such as Gryllotalpidae (mole crickets) and Acrididae (grasshoppers); Siphonapteran pests such as Pulex irritans (human flea), *Ctenocephalides felis* (cat flea) and *Ctenocephalides canis* (dog flea); Anopluran pests such as *Pediculus humanus corporis* and *Phthirus pubis* (crab louse); Isopteran pests such as *Reticulitermes speratus* and *Coptotermes formosanus*; Acarina such as Tetranychidae (spider mites) [e.g. *Tetranychus urticae* (two-spotted spider mite), Tetranychus kanzawai (Kanzawa spider mite), *Panonychus citri* (citrus red mite), *Panonychus ulmi* (European red mite) and Oligonychus spp.], Eriophyidae [e.g. Aculops pelekassi (pink citrus rust mite) and *Calacarus carinatus* (purple tea mite)], Tarsonemidae [e.g. *Polyphagotarsonemus latus*], Tenuipalpidae (false spider mites), Tuckerellidae, Ixodidae [e.g. *Haemaphysalis flava* (Japanese tick), *Haemaphysalis flava* (yellow tick), *Ixodes ovatus* and *Ixodes persulcatus*], Acaridae [e.g. *Tyrophagus putrescentiae* (copra mite)], Dermanyssidae [e.g. *Dermatophagoides farinae* (American house dust mite), *Dermatophagoides ptrenyssnus*], Cheyletidae [e.g. *Cheyletus eruditus, Cheyletus fortis, Cheyletus malaccensi* and *Cheyletus moorei*] and chicken mites]; and Nematoda such as *Pratylenchus coffeae* (coffee root-lesion nematode), *Pratylenchus fallax, Pratylenchus loosi, Pratylenchus vulnus* (walnut root-lesion nematode), *Heterodera glycines* (soybean cyst nematode), *Glohodera rostochiensis* (potato cyst nematode), *Meloidogyne hapla* (northern root-knot nematode) and *Meloidogyne incognita* (southern root-knot nematode).

In the present pesticidal method, each of pyriproxyfen or its formulation and chlothianidine or its formulation can be used simultaneously, but it is convenient to use the present pesticidal composition in which pyriproxyfen and chlothianidine are mixed with each other in advance.

The present pesticidal composition comprises pyriproxyfen and chlothianidine as active ingredients and usually further comprises an inert carrier. The inert carrier can be solid carriers, liquid carriers and the like which are utilized for usual pesticidal formulations. The present pesticidal composition can optionally comprise formulation auxiliaries such as surfactant, dispersant, adhesive agent, stabilizer and propellant to be formulated to oil solution, emulsifiable concentrates, wettable powders, flowables such as aqueous suspension and aqueous emulsion, microcapsule formulation, spot-on formulation, pour-on formulation, shampoo formulation, granules, dusts, aerosol, ULV formulation, poison bait, sheet formulation and resin formulation.

The total amount of pyriproxyfen and chlothianidine in the present pesticidal composition is usually 0.01 to 90% by weight, preferably 0.1 to 80% by weight.

Examples of the solid carrier include fine powders and granules of clays such as kaolin clay, diatomaceous earth, bentonite, Fubasami clay and terra alba; synthetic hydrated silicon oxide; talc and the like; ceramics; the other inorganic minerals such as sericite, quartz, sulfur, activated carbon, calcium carbonate and hydrated silica; and chemical fertilizers such as ammonium sulfate, ammonium phosphate, ammonium nitrate, urea and ammonium chloride. Examples of the liquid carriers include water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosene and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloroethane, trichloroethane and carbon tetrachloride; dimethyl sulfoxide; and vegetable oils such as soybean oil and cottonseed oil.

Further, the present composition may be formulated by added a propellant such as flon gas, butane gas, liquefied petroleum gas, dimethyl ether and carbon dioxide thereto.

Examples of the surfactant include alkyl sulfate ester salts, alkylsulfonate salts, alkylarylsulfonate salts, alkylaryl ethers and polyoxyethylenated derivatives thereof, polyethyleneglycol ethers, polyvalent alcohol esters and sugar alcohol derivatives.

Examples of the other auxiliaries such as adhesive agents and dispersants include casein; gelatin; saccharides such as starch, gum arabic, cellulose derivatives and alginic acid; lignin derivatives; bentonite; and synthetic water-soluble polymers such as polyvinyl alcohol, polyvinylpyrrolidone and polyacrylic acids. Further, stabilizers including PAP (isopropyl acid phosphate), BHT (2,6-di-tert-butyl-4-methylphenol), BHA (2-tert-butyl-4-methoxyphenol and 3-tert-butyl-4-methoxyphenol), vegetable oils, mineral oils, fatty acids and fatty acid esters can be utilized as formulation auxiliaries.

Examples of the base materials for the poison bait include bait ingredients such as grain powder, vegetable oils, sugars and crystalline cellulose; antioxidants such as BHT and nordihydroguaiaretic acid; substances for preventing erroneous eating from children and pets such as red pepper powder; and attractants such as cheese flavor, onion flavor, leek flavor and peanut oil.

Examples of the base materials for resin formulations include olefin polymers, vinyl chloride polymers and polyurethanes. To these base materials, there can be added, if necessary, plasticizers such as phthalates and stearic acid; pest attractants such as pheromones; coloring agents with pest-attractive colors; and so on.

The resin formulations can be obtained by kneading the active ingredients into the base materials with a conventional kneader and then forming by injection, extrusion or compression molding. Further, they can be also obtained by supporting the active ingredients on the base materials which do not contain the active ingredients by impregnation, coating, printing or the like. In the operation, the active ingredients may be used in the form of oil solutions, emulsifiable concentrates, flowables or their dilutions. The resin formulations thus obtained can be formed through further steps, if necessary, such as shaping and cutting, into plates, films, tapes, nets, strings or the like, and can also be formed into sheets for mulching, attractive strings, supports for horticultural use, sheet formulations, wrapping films, animal collars and ear tags for animals.

The flowable formulations of the present pesticidal composition usually contain 1–75% by weight of the active ingredients, 0.5–15% by weight of dispersants, 0.1–10% by weight of suspension aids (e.g., protective colloids, thixotropy-conferring compounds), 0–10% by weight of auxiliaries (e.g., antifoaming agents, rust preventives, stabilizers, spreading agents, penetration aids, antifreezing agents, antibacterial agents, antifungal agents). The replacement of water with oils in which the active ingredients can hardly be dissolved makes it possible to produce oily suspensions. As the protective colloids, there can be used, for example, gelatin, casein, gums, cellulose ethers, polyvinyl alcohol and the like. The thixotropy-conferring compounds may include, for example, bentonite, alminum magnesium silicate, xanthan gum, polyacrylic acid and so on.

In the present pesticidal composition and the present pesticidal method, the other insecticide, nematocide, acaricide, repellent, fungicide, herbicide, plant growth regulator, synergist, fertilizer, soil improving agent or animal food may be used simultaneously.

Examples of the insecticide, nematocide and acaricide include pyrethroid compounds such as permethrin, cypermethrin, fenvarelate, esfenvarelate, fenpropathrin, biphenthrin, deltamethrin, fluvalinate, flucythrinate, allethrin, d-allethrin, prallethrin, cyphenothrin, phenothrin, resmethrin, tefluthrin, empenthrin, acrinathrin, cyhalothrin, cyfluthrin, etofenprox, halfenprox, silafluofen, tralomethrin, cycloprothrin, esbiothrin, transfluthrin, terallethrin, imiprothrin and 1-ethynyl-2-fluoro-2-pentenyl 3-(2,2-dichlorovinyl)-2,2-dimethylcyclopropanecarboxylate; organophosphorus compounds such as cyanophos, fenthion, fenitrothion, parathion, methylparathion, pirimiphos-methyl, diazinon, isoxathion, pyridaphenthion, chlorpyrifos, chlorpyrifos-methyl, oxydeprofos, vamidothion, malathion, phenthoate, dimethoate, thiometon, disulfoton, phosalone, phosmet, methidathion, prothiofos, sulprofos, profenofos, azinphosmethyl, pyraclofos, calvinphos, salithion, tetrachlorvinphos, dichlorvos, monocrotophos, naled, dimethylvinphos, propaphos, acephate, metamidofos and ethion; carbamate compounds such as carbaryl, metolcarb, isoprocarb, fenobcarb, propoxur, XMC, ethiofencarb, bendiocarb, pyrimicarb, carbosulfan, carbofuran, benfuracarb, furathiocarb, methomyl, thiodicarb, oxamyl, alanycarb, fenothiocarb, metoxadiazone and fenothiocarb; nitroiminoimidazolidine derivatives; nereistoxin derivatives such as cartap, bensultap and thiocyclam; formamidine derivatives such as amitraz and chlordimeform; phenylpyrazole derivatives such as ethiprole; benzoylphenylurea compounds such as diflubenzuron, teflubenzuron, chlorfluazuron, flufenoxuron, triflumuron, hexaflumuron, lufenuron and novaluron; triazine derivatives such as cyromazine; thiadiazine derivatives such as buprofezine; juvenoid compounds such as methoprene, hydroprene, fenoxycarb and diofenolan; tebufenozide; methoxyfenozide; halofenozide; chromafenozide; chlorofenapir; phenisobromolate; quinomethionate; propargit; fenbutatin oxide; hexythiazox; clofentezine; pyridaben; fenpyroximate; tebufenpyrad; pyrimidifen; polynactin complex; milbemectin; avermectin; ivermectin and azadirachtin.

The present pesticidal method is an application of an effective amount of pyriproxyfen and chlothianidine to pest or a place where pests inhabit. Typical methods are explained as below.

In case of controlling agricultural or forestry pests by the present pesticidal method, the application rate of pyriproxyfen and chlothianidine is usually 10 g to 10000 g, preferably 100 g to 1000 g per 1 hectare at the total amount of the active ingredients. In the present pesticidal method, the concentration is usually 10 ppm to 1000 ppm at the total amount of the active ingredients, when the present pesticidal composition such as emulsifiable concentrates, wettable powders and flowables is diluted with water and applied. Granules and dusts of the present pesticidal composition are applied as they are.

In the present pesticidal method, pyriproxyfen and chlothianidine may be supplied to foliar application to plants those are crops to be protected from agricultural and forestry pests, or soil treatment to the surroundings of the plants for making the active ingredients absorbed from their roots. Soil treatment can also control agricultural and forestry pests those inhabit in soil. Further, the resin formulations formed to sheet or string can be applied by winding around the plants, setting or covering on the soil surface of the surroundings of the plants.

In case of controlling hygienically unfavorable pests by the present pesticidal method, pyriproxyfen and chlothianidine are usually applied indoors and the application rate is 0.1 mg to 1000 mg, preferably 0.5 mg to 200 mg per 1 $m^2$ of the floor at the total amount of the ingredients. The application rate is also 0.01 mg to 300 mg, preferably 0.1 mg to 100 mg per 1 $m^3$ of the space when spraying to the air. The concentration of the applied dilution is usually 0.1 ppm to 10000 ppm at the total amount of the active ingredients, when the present pesticidal composition such as emulsifiable concentrates, wettable powders and flowables is diluted with water and applied. Oil solutions, aerosols, smokings, ULV formulations and poison baits are applied as they are. When the present pesticidal compositions are directly applied to small animals for controlling ectoparasites of the animals such as dogs and cats, they are applied by conventional veterinary methods: for example, as tablets, by feed incorporation, as suppositories or by injection (e.g., intramuscular, subcutaneous, intravenous, intraperitoneal) for systemic control; or by spraying oily or aqueous liquid, by pour-on or spot-on treatment, or as shampoo formulations or resin formulations such as ear tags for non-systemic control. For such direct application to animal bodies, the amounts for application are usually 0.1 mg to 500 mg per 1 kg of the animal weight at the total amounts of the active ingredients.

The amounts or concentrations for application may vary depending upon type of formulations, times, places and methods of application, kinds of pests, degree of damage, and other factors; they can therefore be increased or decreased without limitation to the above ranges.

EXAMPLES

The present pesticidal composition and the present pesticidal method will be further illustrated by the following formulation examples and test examples; however, the present invention is not limited to these examples. In the following formulation examples, part means part by weight.

Formulation Example 1 Emulsifiable Concentrate

Five parts of pyriproxyfen, 5 parts of chlothianidine, 8 parts of polyoxyethylenealkyl aryl ether, 2 parts of sodium alkylarylsulfonate and 80 parts of xylene are uniformly mixed to give an emulsifiable concentrate.

Formulation Example 2 Wettable Powders

Five parts of pyriproxyfen, 10 parts of chlothianidine, 3 parts of sodium alkylbenzenesulfonate, 3 parts of sodium ligninsulfonate and 79 parts of diatomaceous earth are uniformly mixed and pulverized with a jet air mill to give wettable powders.

Formulation Example 3 Dusts

Two parts of pyriproxyfen, 1 part of chlothianidine, 47 parts of talc and 50 parts of clay are uniformly mixed and pulverized to give dusts.

Formulation Example 4 Flowable

Five parts of polyoxyethylene styryl phenyl ether sulfate, 20 parts of 1 wt % aqueous solution of xanthan gum, 3 parts of smectite mineral and 52 parts of water are mixed, to which 5 parts of pyriproxyfen and 15 parts of chlothianidine are added, and the resultant mixture is well stirred and then wet pulverized in a sand mill to give a flowable.

Formulation Example 5 Microcapsule Formulation

Five parts of pyriproxyfen, 5 parts of chlothianidine, 10 parts of phenylxylylethane and 0.5 part of Sumidur L-75 (toluenediisocyanate produced by Sumitomo Bayer Urethane Co., Ltd.) are mixed, and the resultant mixture is then poured into 20 parts of 10 wt % aqueous gum arabic solution, followed by stirring in a homomixer to give an emulsion with an average particle diameter of 20 $\mu$m. Two parts of ethylene glycol is added to the emulsion and the reaction is allowed to proceed in a water bath at 60° C. for 24 hours to give a microcapsule slurry. Separately, 0.2 part of xanthan gum and 1.0 part of Veegum R (aluminum magnesium silicate produced by Sanyo Chemical Industries, Ltd.) are dispersed in 56.3 parts of ion-exchanged water to give a viscocity-improver solution.

Finally, 42.5 parts of the above microcapsule slurry and 57.5 parts of the above viscocity-improver solution are mixed to give a 10% microcapsule formulation.

Formulation Example 6 Oil Solution

One-tenth (0.1) part of pyriproxyfen and 0.5 part of chlothianidine are dissolved in a mixture of 5 parts of xylene and 5 parts of trichloroethane, and the resultant solution is then mixed with 89.9 parts of deodorized kerosene to give an oil solution.

Formulation Example 7 Poison Bait

Fifteen milligrams (15 mg) of pyriproxyfen and 5 mg of chlothianidine are dissolved in 0.5ml of acetone, and the resultant solution is then uniformly mixed with 5g of solid feed powder for animals (Breeding Solid Feed Powder CE-2 produced by Japan Clea Co., Ltd.). Air drying the mixture to remove the acetone gives a poison bait.

Formulation example 8 Resin formulation

Two parts of pyriproxyfen and 1 part of chlothianidine are kneaded with 98 parts of polyethylene resin (Sumikathene produced by Sumitomo Chemical Co., Ltd.) in a pressure kneaer, followed by pelletizing. The pellets are extruded at 160° C. to 180° C. with an inflation film making machine to give a film-shaped resin formulation with a thickness of 0.1 mm. Formulation example 9 Heating smoke formulation Fifty milligrams (50 mg) of pyriproxyfen and 50 mg of chlothianidine are dissolved in a suitable amount of acetone. The resultant solution is then absorbed in a porous ceramic plate with a size of 4.0 cm×4.0 cm to give a heating smoke formulation.

Test Example 1

Cabbage seedlings planted in 3 ounces plastic cup were placed in a net cage containing many living silverleaf whiteflies for 24 hours, so that many silverleaf whiteflies became parasitic on the cabbage seedlings. A designated amount of each of pyriproxyfen EC (commercial name, Lano emulsifiable concentrate : produced by Sumitomo Chemical Co., Ltd.), chlothianidine EC (emulsifiable concentrate prepared by mixing 10 parts of chlothianidine, 8 parts of polyoxyethylenealkyl aryl ether, 2 parts of sodium alkylarylsulfonate and 80 parts of xylene), and the present invention composition prepared according to formulation example 1 was diluted with water, and then sprayed over the cabbage seedlings with a spray gun. The number of silverleaf whiteflies (i.e., the total number of adults and larvae) surviving on the cabbage seedlings was examined just before and after 8 days from the treatment. The test results are shown in table 1.

TABLE 1

| Compound | Concentration (ppm) | Number of surviving insects/pot | |
|---|---|---|---|
| | | before | after 8 days |
| pyriproxyfen | 50 | 65 | 21 |
| chlothianidine | 50 | 66 | 70 |
| pyriproxyfen + chlothianidine | 12.5 + 12.5 50 + 50 | 96 74 | 0 0 |
| No treatment | — | 96 | 88 |

Test Example 2

Cabbage seedlings planted in 3 ounces plastic cup were placed in a net cage containing many living silverleaf whiteflies for 24 hours, so that many silverleaf whiteflies became parasitic on the cabbage seedlings. A designated amount of each of pyriproxyfen EC. (commercial name, Lano emulsifiable concentrate: produced by Sumitomo Chemical Co., Ltd.), chlothianidine EC (emulsifiable concentrate prepared by mixing 10 parts of chlothianidine, 8 parts of polyoxyethylenealkyl aryl ether, 2 parts of sodium alkylarylsulfonate and 80 parts of xylene), and the present invention composition prepared by mixing the pyriproxyfen EC with chlothianidine EC at 10:1 and 1:10 by weight was diluted with water, and then sprayed over the cabbage seedlings with a spray gun. The number of silverleaf whiteflies (i.e., the total number of adults and larvae) surviving on the cabbage seedlings was examined just before and after 8 days from the treatment. The test results are shown in table 2.

TABLE 2

| Compound | Concentration (ppm) | Number of surviving insects/pot | |
|---|---|---|---|
| | | before | after 8 days |
| pyriproxyfen | 10 | 81 | 29 |
| | 10 | 62 | 73 |
| Pyriproxyfen + chlothianidine | 10 + 1 1 + 10 | 76 45 | 1 0 |
| No treatment | — | 70 | 135 |

Industrial Applicability

As shown above, the pesticidal composition of the present invention is useful for controlling various pests, and various pests can be effectively controlled by the pesticidal method of the present invention.

What is claimed is:

1. A pesticidal composition which comprises 4-phenoxyphenyl 2-(2-pyridyloxy)propyl ether and (E)-1-

(2-chlorothiazol-5-ylmethyl)-3-methyl-2-nitroguanidine as active ingredients.

2. A pesticidal composition according to claim 1, wherein the content ratio of 4-phenoxyphenyl 2-(2-pyridyloxy) propyl ether and (E)-1-(2-chlorothiazol-5-ylmethyl)-3-methyl-2-nitroguanidine in the composition is a ratio which can give synergistic effect.

3. A pesticidal composition according to claim 1, wherein the weight ratio of 4-phenoxyphenyl 2-(2-pyridyloxy)propyl ether and (E)-1-(2-chlorothiazol-5-ylmethyl)-3-methyl-2-nitroguanidine in the composition is in the range of from 100:1 to 1:30.

4. A method for controlling pests which comprises applying an effective amount of 4-phenoxyphenyl 2-(2-pyridyloxy)propyl ether and (E)-1-(2-chlorothiazol-5-ylmethyl)-3-methyl-2-nitroguanidine to pest or place where pest inhabits.

5. A method for controlling pests according to claim 4, wherein the weight ratio of 4-phenoxyphenyl 2-(2-pyridyloxy)propyl ether and (E)-1-(2-chlorothiazol-5-ylmethyl)-3-methyl-2-nitroguanidine is in the range of from 100:1 to 1:30.

6. A method for controlling pests harmful to crop which comprises applying an effective amount of 4-phenoxyphenyl 2-(2-pyridyloxy)propyl ether and (E)-1-(2-chlorothiazol-5-ylmethyl)-3-methyl-2-nitroguanidine to plant or soil.

7. A method for controlling pests according to claim 6, wherein the weight ratio of 4-phenoxyphenyl 2-(2-pyridyloxy)propyl ether and (E)-1-(2-chlorothiazol-5-ylmethyl)-3-methyl-2-nitroguanidine is in the range of from 100:1 to 1:30.

8. A method for controlling ectoparasites of animal which comprises applying an effective amount of 4-phenoxyphenyl 2-(2-pyridyloxy)propyl ether and (E)-1-(2-chlorothiazol-5-ylmethyl)-3-methyl-2-nitroguanidine to host animal.

9. A method for controlling pests according to claim 8, wherein the weight ratio of 4-phenoxyphenyl 2-(2-pyridyloxy)propyl ether and (E)-1-(2-chlorothiazol-5-ylmethyl)-3-methyl-2-nitroguanidine is in the range of from 100:1 to 1:30.

* * * * *